United States Patent [19]
Rector et al.

[11] Patent Number: 5,517,251
[45] Date of Patent: May 14, 1996

[54] ACQUISITION OF VIDEO IMAGES SIMULTANEOUSLY WITH ANALOG SIGNALS

[75] Inventors: David M. Rector, West Los Angeles; Ronald M. Harper, Los Angeles, both of Calif.

[73] Assignee: The Regents of the University of California, Oakland, Calif.

[21] Appl. No.: 234,300

[22] Filed: Apr. 28, 1994

[51] Int. Cl.$^6$ ................................................. H04N 7/087
[52] U.S. Cl. ........................... 348/476; 348/588; 348/598
[58] Field of Search .................................. 348/476, 473, 348/588, 598, 239, 584; H04N 7/087

[56] References Cited

U.S. PATENT DOCUMENTS

| | | | |
|---|---|---|---|
| 3,798,366 | 3/1974 | Hunt et al. | 348/165 |
| 3,993,861 | 11/1976 | Baer | 348/473 |
| 4,018,986 | 4/1977 | Wilk | 348/473 |
| 4,051,522 | 9/1977 | Healy et al. | 348/473 |
| 4,186,413 | 1/1980 | Mortimer | 348/473 |
| 4,218,707 | 8/1980 | Reed et al. | 348/164 |
| 4,807,031 | 2/1989 | Broughton et al. | 348/473 |
| 4,855,827 | 8/1989 | Best | 348/473 |
| 4,876,600 | 10/1989 | Pietzsch et al. | 348/588 |
| 4,969,041 | 11/1990 | O'Grady et al. | 348/473 |

OTHER PUBLICATIONS

David J. Sirag, IFF Phys—Routines for IFF physical data files, 1989.

Primary Examiner—Victor R. Kostak
Attorney, Agent, or Firm—Merchant, Gould, Smith, Edell, Welter & Schmidt

[57] ABSTRACT

A system for processing multiple signals. The system includes a receiver for receiving a video signal representative of a camera image, the video signal being represented as multiple horizontal lines in a video frame, a receiver for receiving multiple analog signals, the analog signals being representative of different analog inputs, a buffer for digitally double buffering at least some of the analog signals, wherein the buffer effects repetition of analog signals within a single video image frame, repeats sampling of the analog signals more than once within a single video frame and the digitization enhances recovery of the signal resolution of the analog signal with greater frequency and representation than an analog signal on a video signal. The system also comprises a mixer for mixing the analog signals with the video signal whereby the analog signals are contained on at least some of the horizontal lines of the video frame, and an output for outputting the mixed analog and video signals.

35 Claims, 5 Drawing Sheets

ACQUISITION OF VIDEO IMAGES SIMULTANEOUSLY WITH ANALOG SIGNALS

This invention was in part supported by NIH Grant No. HL-22418, and the government may have certain rights in this invention.

BACKGROUND

Data acquisition for long-term monitoring of physiological signals and video signals of patients is exceedingly valuable in the current medical environment.

This invention relates to obtaining, storing, and analyzing video and analog signals. In particular the invention is concerned with the simultaneous processing of such signals.

A need exists for acquisition of dynamic video images of physiological processes of a patient simultaneously with electrophysiological signals of the patients.

Correlation of both the video signals and the physiological signals at high temporal resolution is valuable. The rapid computer retrieval of these signals, is also a requirement.

Synchronous video and analog signal acquisition are required for visual determination of sleep state, body or limb position, or somatic activity together with collection of electroencephalographic, electrocardiographic, respiratory or electromyographic activity. Examination of cellular optical properties that are associated with unique electrophysiological patterns is also a consideration.

Concurrent video and analog recordings are useful for evaluation of electrophysiological signals associated with sleep disorders, simultaneous monitoring of seizure activity and limb movements, and comparison of electrophysiological signals with changes in optical properties of neural tissue.

A need also exists for concurrent recording of a hundred or more channels of EEG.

Typically, video images and physiological signals are acquired and stored on separate media with common synchronizing signals. Often physiological data are captured in digital format, with video data stored on analog media. During analysis, the signals are temporally aligned using synchronizing pulses. However, processing data with analog technology is cumbersome and time consuming. If frame accuracy is required, synchronization demands specialized video recorders. Even if video data are stored digitally, synchronizing digitized physiological signals with images is often difficult.

An ideal physiological monitoring system for acquiring data, particularly from sleeping infants or epileptic subjects, would have facilities for collecting multiple channels of physiological signals gathered at high temporal resolution. The system would also store video indications of body position, movements, or other somatomotor characteristics. Such characteristics are usually noted by an observer using handwritten notes or specially-coded signals.

Observer-based encoding methods lack detailed description, suffer from errors introduced by fatigue and observational lapses, and lack high temporal resolution. Behavioral measurements should minimally interfere with normal physiological functions, and should provide near-instantaneous access to both video and physiological data on a computer-readable format for analysis.

The need also exists for a video system to monitor infants at risk for the sudden infant death syndrome (SIDS). Information pertaining to body position during the night, extent of body covering, and patterns of movements are of special interest. At the same time, a need exists to gather multiple channels of physiological data at high temporal resolution. Multiple channels are required for adequate identification of state and to appropriately identify interactions between several physiological systems which may fail in SIDS victims.

Recording of epileptic patients would also greatly benefit by acquisition of video images of ictal episodes simultaneously with physiological signal acquisition.

The classical procedure for simultaneous video and physiological signal acquisition usually stores video images on videotape media, and physiological signals on other media.

In many studies, the physiological and video signals are stored on separate tapes. The two signal sources are then coordinated by using a synchronizing code. However, integration of physiological signals with video data requires substantial manual intervention which is costly, frequently not accurately time-synchronized, and exceptionally unwieldy to use.

Occasionally, signals from a video camera viewing the subject is mixed with signals from a second video camera viewing the polygraph record. The combined video signals are displayed on a split screen, and video-taped for correlation of image and electrophysiological events. Procedures which use videotape as a primary medium for storage of video signals have several handicaps. Such storage is typically in a non-computer retrievable format, and the physiological signals lack sufficient resolution for analysis.

The known systems for obtaining and recording signals from different sources and rendering them recoverable with a video signal suffer limitations.

A need clearly exists for improved system to achieve these objectives.

SUMMARY

This invention provides an effective system for acquiring and interleaving a large number of physiological channels together with a video signal. The interleaved data can be stored on conventional videotape.

According to the invention there is provided a system and method for processing multiple signals. The signals include a video signal representative of a camera image and the video signal is represented by multiple horizontal lines. There are also multiple analog signals, the analog signals being representative of different analog inputs.

Further, according to the invention, there is an inexpensive means and method for mixing the analog signals with the video signal whereby the analog signals are contained on at least some of the horizontal lines of the video signal. There are also means provided for outputting the mixed video signal and analog signals. Since the video and analog data are mixed before digitization, the procedure reduces the overall complexity of the acquisition process.

The mixed video and analog signals are integrated in a manner such that the output can be digitized and stored on computer or stored on video tape.

Analog signals are preferably represented on the video image as a vertical band, the vertical band being composed of multiple horizontal lines. The band may be of any selected thickness and can be varied as necessary. The band can be located in a selected portion of a screen representing the video signal.

Buffering can be used so that the analog signal can be repeated a selected multiple number of times within each screen representative of the video signal for a selected frame. As such, the analog signals can be repeated or refreshed a multiple selected number of times within each video frame.

In one preferred form of the invention, the mixed video images and physiological signals can be stored together in a computer-retrievable format with 16 ms accuracy using a framegrabber and a computer.

Also according to the invention there is means for and a procedure of integrating digitized video and digitized physiological analog signals on a computer-readable format within a single file. The procedure simplifies analysis of signals which require synchronization and integration of both video and physiological data for interpretation.

The invented method is useful for clinical monitoring, and can also be applied to microscopic or videostroboscopic applications, where video events require high temporal resolution for correlation with electrical events.

The signal acquisition package is integrated with several analytic packages for a variety of time-series analyses, non-linear manipulations and statistical procedures.

The invention is further described with reference to the accompanying drawings.

DRAWINGS

DESCRIPTION

A system for processing multiple signals comprises means for receiving a video signal representative of a camera image. The video signal is represented by pixels on horizontal lines.

There are also means for receiving multiple analog signals. The analog signals are representative of different analog inputs, and preferably physiological data.

Means is provided for mixing in a multiplexer the analog signals with the video signal. The analog signals are contained on at least some of the horizontal lines of the video signal. Means is provided for outputting the mixed integrated video signal and analog signals.

The means for outputting the integrated signal is selectively at least one of a video digitizer onto which the video signal and analog signals have been integrated and mixed. Additionally or alternatively, the integrated signal can be stored on a video recorder, and/or tape, and/or stored on a host computer.

The analog signal is represented by a vertical band as portion of the video image on a screen. Each line on the vertical band would be representative of a different analog signal. Where there are 240 horizontal lines representing the video image, there can be up to 240 analog signals. The intensity of the horizontal line on the portion of the band would be representative of the intensity of the analog signal. In this manner the analog signals are integrated into the video signal. Since the video signal is refreshed every 60 cycles per second, the analog signals are similarly refreshed every 60 cycles per second.

In a first situation where it is necessary to refresh the analog signal more frequently, the number of lines representative of the video signal is divided to repeat a selected number of analog signals for each video screen representation. Thus, a first predetermined number of lines, namely 240 would represent the video signal. A second predetermined number of signals, namely 240 can represent 240 analog signals.

Figure 5:
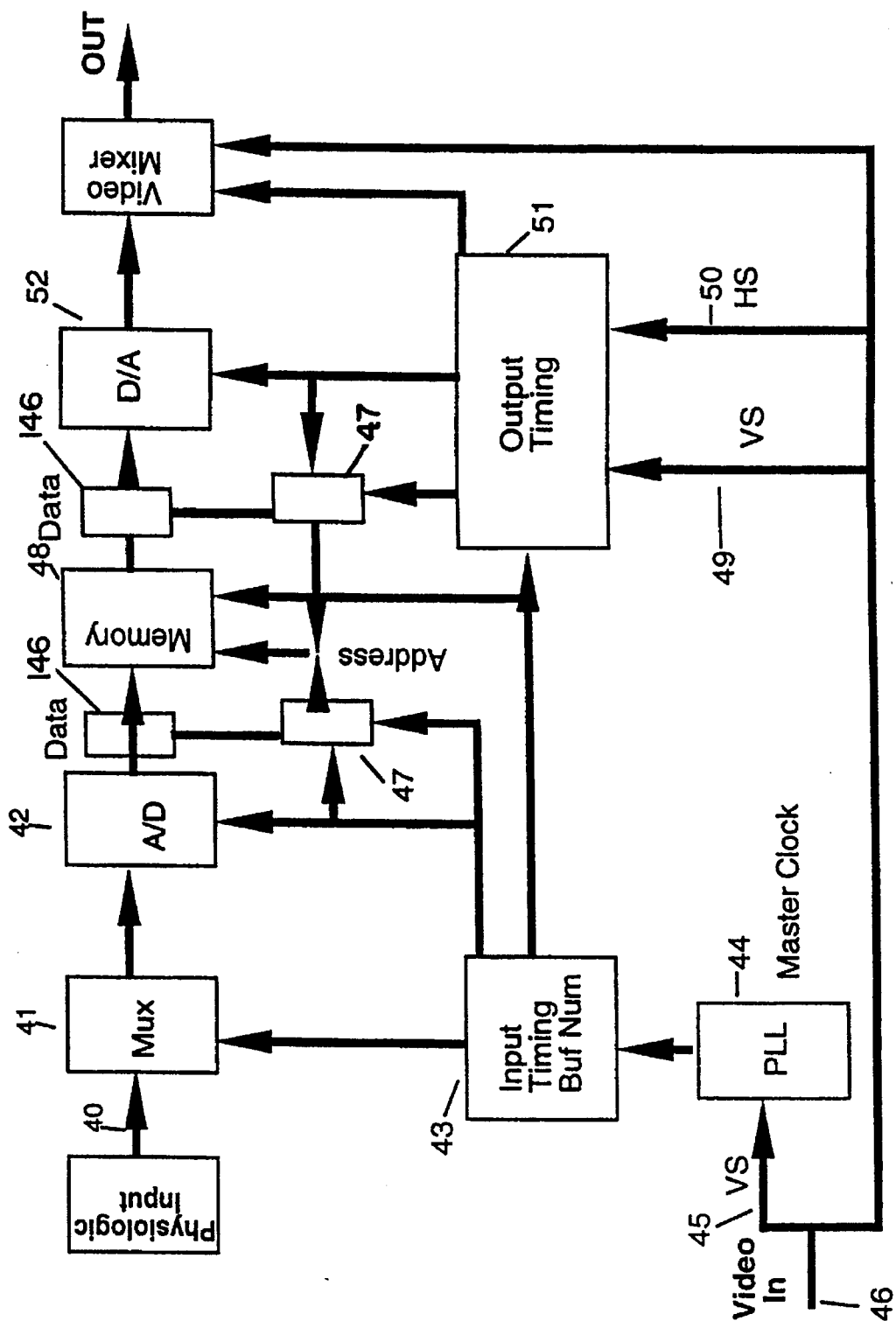
FIG. 5 illustrates a schematic diagram with a buffer system for use with the circuit.

In a second situation, a third number of lines, being a lesser number than the second predetermined number can represent the analog signals. Thus, 120 analog signals can be represented, each, twice in the 240 lines of the video signal. Thus, the analog signals are inputted at twice the frequency of the video signal. Different multiples, namely more, 4, 8 or 16 repetition times can be used, as necessary. The greater the frequency of repetition, the fewer the number of analog signals available per video screen frame. A disadvantage is a 2 msec gap between fields which causes a timing error for reconstructing the analog signals with equal sample intervals. The diagram in FIG. 5 illustrates signal buffering to solve timing errors.

Example of Multiplexed Video Signals and Audio Signals

Figure 1:
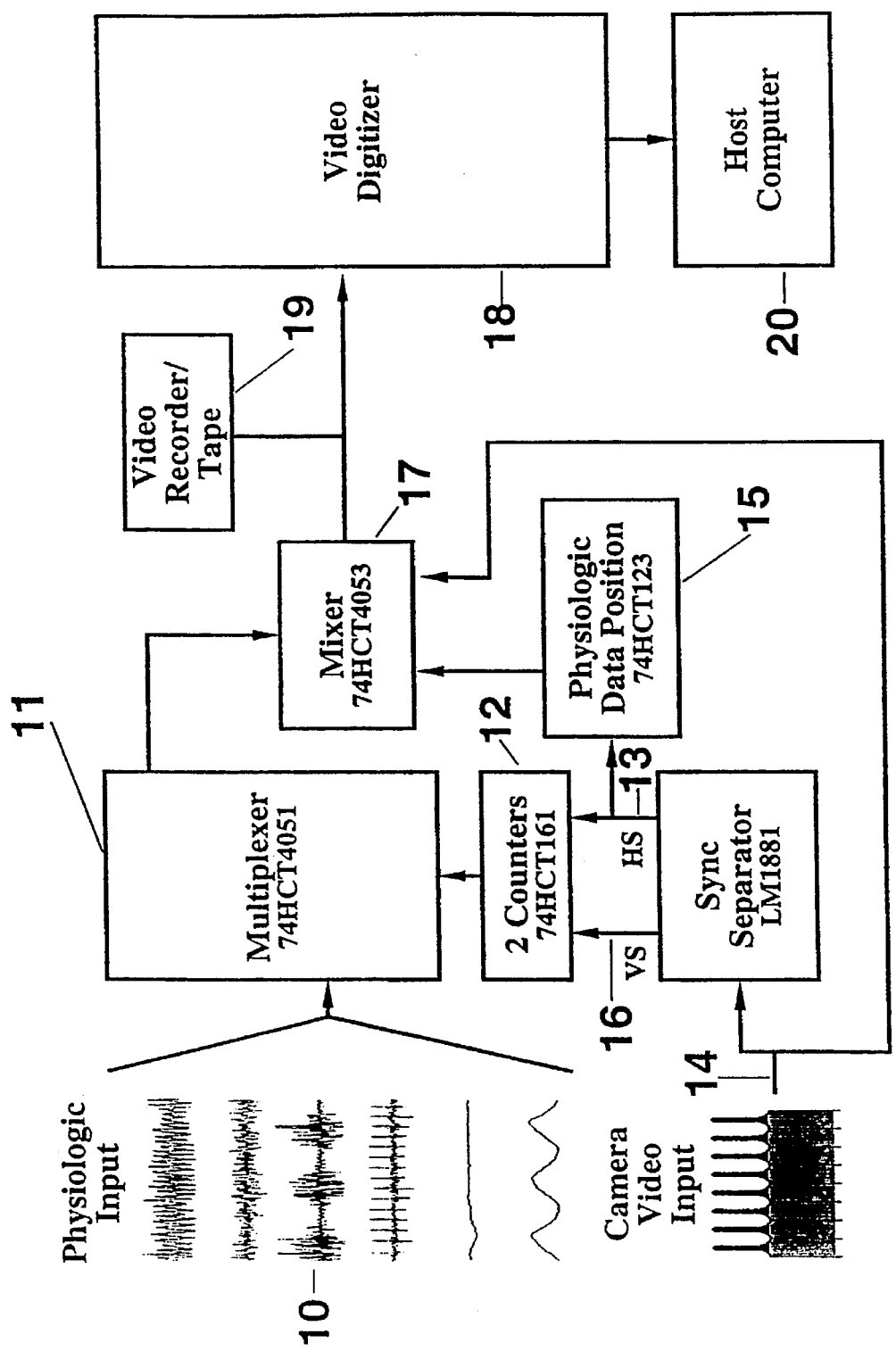
FIG. 1 is a block diagram of a multiplexer system illustrating the circuitry for simultaneous acquisition of video and electrophysiological input signals.

In the system illustrated in FIG. 1, up to 8 physiological signals 10 can be selected by a single analog-switch multiplexer 11, which is selected by two 4-bit binary counters 12. Up to 240 channels can be acquired with additional multiplexer circuits.

Horizontal synchronizing signals (HS) 13 from the camera video input 14 are used to increment the counters 12. The signal 13 serves as a reference for the physiological data position circuit 15 to limit the portion of the horizontal line which is occupied by physiological data. Vertical synchronizing signals (VS) 16 are used to reset the counters 12.

A mixer 17 is an analog-switch, which selects either video or physiological data. The output of the mixer 17 is fed into the video digitizer 18, which samples video and physiological data simultaneously. Alternatively and/or additionally, the output of the mixer 17 can be directed to a conventional video recorder 19. The video digitizer feeds a host computer 20 for signal analysis as required.

Figure 2:
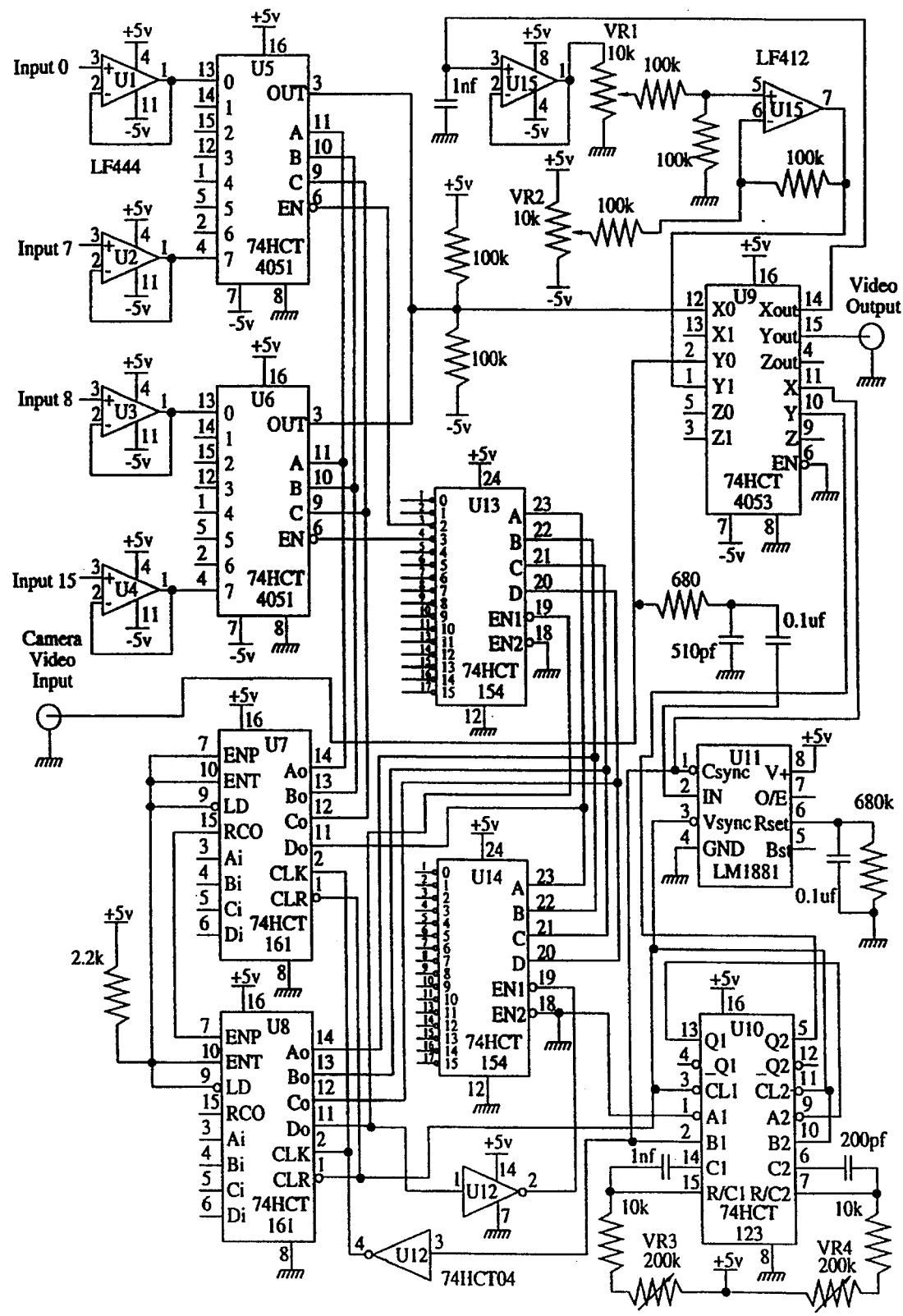
FIG. 2 is a schematic diagram of the multiplexer circuit configured for 16 input channels.

In FIG. 2 buffer amplifiers U1 through U4 are used to isolate the physiological signals from circuit switching noise. Analog switches U5 and U6 are 8 channel analog switches which select the physiological inputs in sequential order, based on the state of the counters U7 and U8. The counters are driven by the horizontal synchronizing pulses from sync-separator U11. Two decoders, U13 and U14, are used to select 1 of up to 30 multiplexer chips.

The first two decoder outputs are not used, since the video digitizer or tape recorder may not process the first 16 horizonal lines which occur after the vertical synchronizing pulse. Each multiplexer chip can select one of eight physiological inputs. Thus, a total of 240 inputs can be incorporated by using a total of thirty multiplexer circuits. Since the vertical synchronizing pulse resets the counter, each video field begins with physiological channel 0.

The outputs of the multiplexers are selected for a short time by the X switch of the mixer which contains three independent switches: X, Y, and Z. The X switch is used for the sample-and-hold circuit, the Y switch is used for the mixer, and the Z switch is not used. During the horizontal pulse, the X switch is closed, such that the selected physiological channel is sampled by the sample and hold circuit U15.

The amplitude of the sample-and-hold output can be adjusted with VR1, and the offset adjusted with VR2. A re-triggerable one-shot U10 is used to select the portion of the video screen occupied by the physiological channels. The left screen position is selected by VR3, and the duration of the displayed sample is selected by VR4. When the first half of the one-shot U10 is triggered by the horizontal synchronizing pulse from the sync-separator U11, the one-shot U10 waits a specified time, set by VR3, to turn on (physiological data selected) the Y switch of the mixer U9. This selects the output to be either camera video, or multiplexed physiological data. The second half of the one-shot U10 waits a specified time, set by VR4, until switch Y is turned off, and the video data is selected.

The system consists of several components. The first component detects horizontal synchronizing pulses from the input video signal of an NTSC (National Telecommunications Standards Committee) camera used to acquire images. The horizontal synchronizing pulses increment an eight-bit counter that sequentially selects each of 240 electrophysiological input analog signal channels to a sample-and-hold multiplexer.

The output of the multiplexers U5 and U6 represents a portion of each horizontal line composed of the sampled value from each electrophysiological channel. The multiplexer output is mixed with the video signal. The intensity of a portion of each horizontal scan line represents the amplitude value of one physiological signal. The remainder of the scan line contains video information. Typically, only a small portion of the video scan line is used to represent the physiological data.

The mixed signal is then fed to a conventional video recorder for storage or to the input of a video digitizer 18. This simultaneously digitizes the physiological and video data as a 256 (8 bit) grey level signal.

An LM1881 (National Semiconductor, Santa Clara, Calif.) sync-separator U11 detects vertical synchronizing pulses (VS) and horizontal synchronizing pulses (HS) from the camera video input signal. The horizontal synchronizing pulses are connected to the clock input of two four-bit counters U7 and U8. The falling edge of the horizontal synchronizing pulse selects one of the electrophysiological input signals through two or more multiplexer switches U5 and U6.

Two sixteen-channel decoders U13 and U14 are used to select the appropriate multiplexer chips U5, U6. The vertical synchronizing pulses reset the counters U7 and U8 so that the count begins on the same channel for each field of the video signal.

The outputs of the multiplexers are sampled by a switch U9. These outputs are amplified for adjustment of offset and gain of the physiological signals, and mixed to select either video or physiological data to be placed on the horizontal line. A one-shot circuit U10 is driven by the horizontal synchronizing pulses to select the time window in which each physiological signal occupies the horizontal line.

The digitizer board (Rambrandt, Progressive Peripherals, Denver, Colo.) incorporates a TMS34020 video processing chip (Texas Instruments Inc., Dallas, Tex.) that allows simultaneous acquisition and processing of 24 bit RGB or NTSC video. A large number of different commercial video digitizers can serve these functions.

Once the image is digitized, data on the video portion of the line are transferred to a host computer (A3000, Commodore Business Machines, West Chester, Pa.) together with one pixel from each horizontal line of the physiological data. A wide range of laboratory computers could be used with an appropriate framegrabbing board capable of 8 bits or greater signal digitizing resolution.

An Intel 80486 based computer, 33 MHz or 66 MHz clock rate with a high throughput framegrabber (ComputerEyes/RT; Digital Vision Inc., Dedham, Mass.) is effective to achieve equivalent results. The 486 based processors require a fast-caching hard-disk controller to reduce processor time used for storage device access.

DC Response

To ensure DC response levels, one of the analog input channels is connected to ground. Once a ground reference signal is acquired, the output from other channels is adjusted for DC shifts by a summing amplifier. For digitized data, the output of the physiological channels are offset by the digitized value of the ground reference channel.

Aliasing

The physiological signals are low-pass filtered at 30 Hz before the multiplexer to prevent aliasing. This facilitates monitoring slow-changing or relatively static conditions at the same time as monitoring fast-changing signals. For example, slow changes in temperature or light can be monitored as the ECG signals change.

Data Processing

When the video and physiological data are stored digitally, the IFFPHYS format (Interleaved File Format, Physical Data), a variation of the IFF format (Interleaved File Format, Electronic Arts, San Mateo, Calif.) is used for images, sound, and text storage. Details of the IFFPHYS is disclosed in D. Sirag, IFFPHYS: Interleaved File Formata, Physical Data, by David Sirag of 7215 So Harvest Avenue, Cerritos, Calif. 90701 and obtainable from Internet Number HARPER@AUNIX.LONI.UCLA.EDU, the contents of which are incorporated by reference herein.

This format places specifications for identification and file localization of both video and physiological data, and allows access by a variety of analytic programs across different computer platforms. An analytic routine provides retrieval of selected image frames by frame number and provides basic image analysis processes, such as averaging, image subtraction, and statistical processing of selected or all pixels in an image.

Results

Figure 3A:
FIG. 3A is an illustration of a digitized video image mixed with 240 sampled physiological analog values.
Figure 3B:
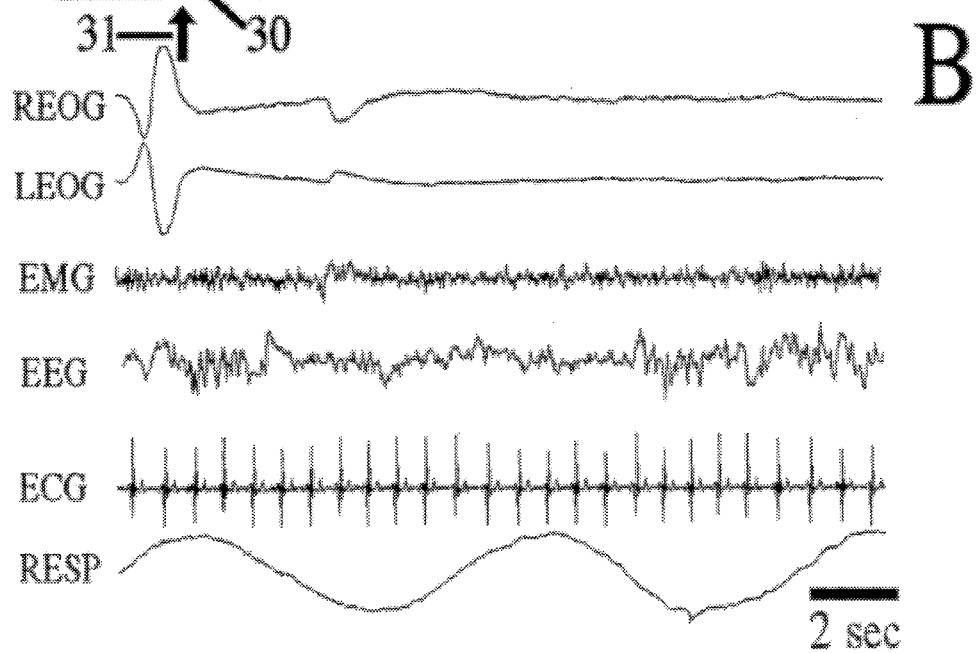
FIG. 3B illustrates six of the multiple reconstructed traces from FIG. 3A calculated by analytic routines from the digitized physiological data, sampled at 60 Hz.

Up to 240 channels are recorded together with video images at a temporal resolution of 60 fields per second. A sample multiplexed image is shown in FIG. 3A. The analog data appear as short lines 30 towards the left portion of the field in FIG. 3A indicated by the arrow 31. The position of the sampled values can be placed anywhere in the video field 32. The intensity of each line 30 represents the amplitude of the corresponding physiological channel. The width of the band or strip 33 can be varied as required. After the multiplexed images were digitized, an analytic routine separated physiological data from the video data. Sample output traces are shown in FIG. 3B.

The system and circuitry are used for simultaneous acquisition of up to 240 channels of electrophysiological data with video signals.

If computer storage is not required, the interleaved signals are saved on conventional videotape recorders and retrieved through a de-multiplexing circuit or digitized at a later time.

The analog-to-digital conversion resolution of typical video framegrabbers is 8 bits (one part in 256), which is comparable to the signal resolution obtained on FM-based instrumentation recorders. These recorders provide 44–48 Db signal to noise ratio. Within a 2 V signal range, the digitizer resolution is better than 10 My, an accuracy adequate for most physiological signals. The resolution requires care in monitoring the dynamic range of data to prevent distortion from coarse sampling resolution, or from exceeding the digitizer input range. A compounding amplifier may be used to convert the signals to log values to improve dynamic range but reduces resolution.

Refreshing & Buffering

A restriction is the sampling rate. This is limited by the 60 Hz field refresh rate of the video signal. This restriction results from the limitation of storing only one sequence of 240 samples per field, namely one channel per line, to ensure equi-spaced samples of the electrophysiological inputs.

The restriction in sample rate is removed with buffering of the incoming physiological signals, as illustrated in FIG. 5.

Double-Buffered Video/Analog Multiplexer

The multiplexer circuit increases the temporal resolution of mixed analog and video signals over the multiplexer of FIG. 2. The circuit of FIG. 2 placed one value from each input channel on the image. This limited the sampling resolution to 60 Hz for each channel. 60 Hz is the combined repetition rate of the two video fields. By digitizing the sampled analog values at regular intervals within the field it is possible to buffer the values in memory for storage. These values are read again during the subsequent field at a faster rate. The values of the second signal are converted back to analog values, and the analog values are mixed with the video signal.

Up to 256 channels of input 40 are selected by a multiplexer 41 and converted to a 12-bit digital word by an analog-to-digital converter 42. The multiplexer 41 is controlled by a counter and timing circuit 43 which is driven at a specific rate determined by a phase-locked-loop circuit 44, which is locked to the vertical sync of the video signal 45. This master clock is an integral multiple of the vertical refresh rate of the video signal 46.

The timing circuit 43 also gates the tristate data buffers 146 and address buffers 47 which store the digitized words into a memory block 48. The memory 48 is divided into two buffers. While one buffer is being filled by the analog-to-digital converter, the second is read out by the output circuit. This implies that the analog data will always be offset in time by one video field.

The vertical and horizontal sync signals 49 and 50 also drive the output timing circuit 51 which reads out the buffer which has just been filed by the analog-to-digital circuit 42. Since the data are stored in digital form in memory 48, the values can be read at a faster rate than they were captured. This allows the digital-to-analog converter 52, the capability to represent each digitized value in any configuration on the output image.

For example, a rectangular area within the video field could be defined such that each horizontal line represents a particular channel. Pixels on the same line can represent each channel at a different point in time. The number of channels and sampling rate is limited only by the number of pixels which are available on the video image, and by the speed of the analog to digital converter.

The data can be encoded onto the video signal in at least two fashions. One process encodes the digital value of the analog signal as a proportionate intensity of the video signal. Each sample would be represented as a single pixel. This procedure is limited by signal-to-noise characteristics of standard video recorders, which for commercial units is approximately 46 db (approximately 7 bits of resolution). Recorders based on S-VHS principles have slightly better characteristics, with approximately 8 bits of resolution.

Another encoding process is to encode each bit as a single "on" or "off" pixel (i.e., full black or full white level). By this means, little degradation of the signal occurs when encoding the digital value of the analog signal onto the video signal. A 12 bit sample, for example, would be represented as a string of 12 pixels, each of which would be "on" or "off". Signal reconstruction is greatly enhanced because the resolution is not limited by the video digitizer.

The buffering adds to the complexity of the circuit. A 60 Hz sampling rate is sufficient for a variety of physiological signals, including respiratory signals, integrated electromyograph signals, movement signals, and EEG signals where the principal focus is activity below 30 Hz. The benefit of this system includes a large channel capacity for low bandwidth signals stored simultaneously with video at low cost.

Compression

The recording time and digital storage capacity required is a function of image size and any compression performed on the video frame. The compression should be lossless to preserve the integrity of the physiological signals. Alternatively, the physiological signals could be extracted before compression. The image size should be sufficiently large to acquire the number of lines required for the physiological inputs; for example, at least 240 lines are needed for 240 physiological channels. The simplest images contain 256 grey levels from a monochrome camera. A color video is possible, but requires 24 bit RGB storage or 12 bit YUV encoding per digitized pixel to preserve the physiological data.

Components

All components for the circuitry are obtained from National Semiconductor, Santa Clara, Calif.

Example of Interleaved Video Signals and Analog Signals

Figure 4:
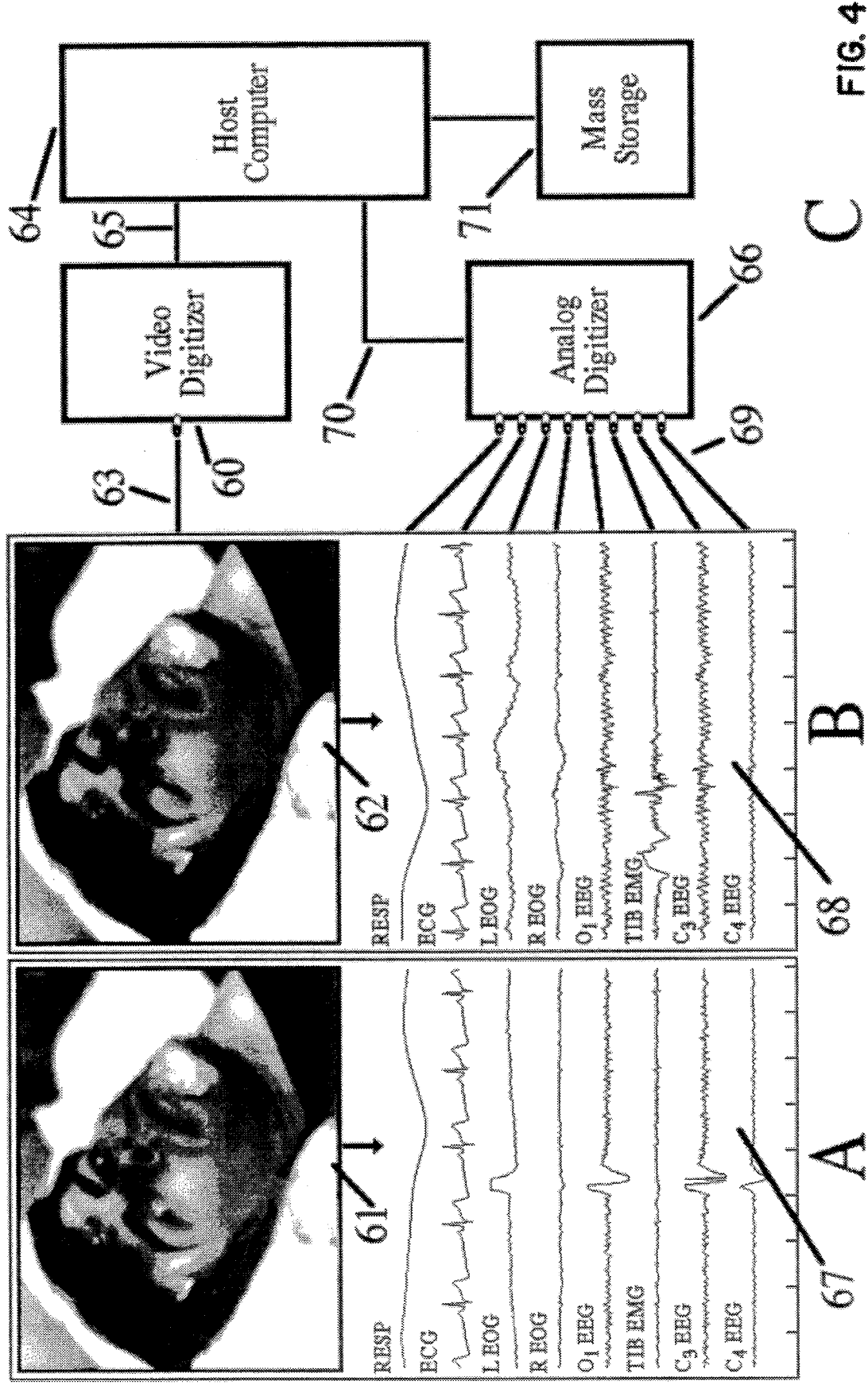
FIG. 4A is a sample playback screen which shows the subject with eyes open. The subject was instructed to look right, causing a deflection in the EOG traces.
FIG. 4B is a sample playback screen which shows the subject with eyes closed. The subject was instructed to move his foot, causing the high frequency burst in the TIB EMG trace.
FIG. 4C illustrates a block diagram of the video and analog acquisition system used with the method as applied in the method of FIGS. 4A and 4B.

In FIGS. 4A and 4B there are two sample playback screens. Tick marks under the physiological traces of FIGS. 4A and 4B indicate 500 ms intervals (A).

The various abbreviations indicate data as follows.

RESP=Respiratory activity via chest wall expansion,

ECG=Electrocardiogram,

EOG=Electro-oculogram,

EEG=Electroencephalogram,

TIB EMG=Tibialis Electromyogram.

The arrows below the image in each example indicate the 16 ms time period during which the images were acquired relative to the electrophysiological signals. Each playback screen of FIGS. 4A and 4B is drawn with 800 by 640 resolution. Each electrophysiological signal is plotted with a maximal 16 pixel amplitude. To achieve higher vertical discrimination of the analog traces, fewer channels could be displayed, leaving more pixels per channel.

The hardware components used for the example illustrated in FIGS. 4A and 4B are outlined in FIG. 4C. The video digitizer 60 samples and compresses the images 61 and 62 from the video signal 63, and sends the data to the host computer 64 over the system bus 65. The analog digitizer 66 samples the electrophysiological signals 67, 68 which are fed through lines 69 to the digitizer 66. The analog signals are digitized and the data is transmitted over the parallel port 70. The host computer 64 interleaves the two signals, and stores the digital information as a single file on a mass storage device 71.

The procedure incorporated a microprocessor-based analog acquisition subsystem, a video framegrabber/processor board, a laboratory computer which served as host for the video board, and a large-capacity mass storage device.

The framegrabber portion of the video board was an NTSC (National Telecommunications Standards Committee) device, capable of realtime digitizing at 60 fields/sec (Progressive Peripherals and Software, Denver, Colo.). The board contained a TI34020 processor (Texas Instruments Inc., Dallas, Tex.), math co-processor, 8 megabytes video ram, and 4 megabytes dynamic ram. A large number of comparable off-the-shelf boards are available.

The board was used with an A3000 personal computer equipped with a Motorola 68030 or 68040 processor (Motorola Semiconductor Products Inc., Phoenix, Ariz.), modest amounts (2–4 megabyte) of memory, and a large mass storage device, typically a 2.5 gigabyte 8 mm helical scan tape. An analog-to-digital converter, currently comprised of input amplifiers and a Motorola 68HC11 processor, was used for analog acquisition, and for data transfer to the host computer over a parallel interface.

Video Acquisition

During a recording, the video signal was acquired with 8-bit (256 levels) grey scale resolution at a maximum 60 fields/sec by the framegrabber. A monochrome camera was used for video which restricts the images to grey scale images. The signal definition, however, was adequate for most observations, particularly at low light levels.

Compression

The video processing board is capable of high speed compression using the JPEG (Joint Photographic Engineering Group) algorithm, which reduces the image by a factor of 20 or more. The JPEG algorithm can be constant or variable, and can be adjusted to alter compression over a wide range of factors, with increasing image quality loss at high degrees of compression. Compression is necessary for conditions of limited storage space and large image size requirements at high acquisition rates (greater than 3 fields/sec).

The compression rate is determined by the acceptable level of image smoothing before identifying features of the image are lost. In some studies, such as imaging of subtle light scattering changes over time, only lossless compression is acceptable. Experiments which require only gross image assessment allow high compression rates; typically, image quality is compromised with compression factors greater than 50. Compression factors under 20 are usually indistinguishable from videotaped storage.

The maximal acquisition rate is determined by many factors including pixel resolution, compression rate, computer processor speed, and average disk write speed. Typically, a 160×100 pixel resolution image is digitized at 3 fields/sec (48,000 bytes/sec) without compression, and is sufficient for distinguishing motor events such as large limb movements. Adequate reconstruction of the video field for identification of body movements can be achieved by this resolution, which reduces the throughput to the mass storage device considerably over higher resolution images. On a 2.5 gigabyte tape drive (capable of transfer rates of 250,000 bytes/sec), this acquisition rate provides storage for 41,667 sec (11.6 hr) of data.

Analog Acquisition

Up to 8 analog signals are multiplexed and digitized under the control of a Motorola 68HC11 processor. An algorithm, developed under the FORTH programming language, stores the digitized values in one of two 8 kilobyte buffers and transfers full buffers over a parallel port to the host computer. Other devices allow for 16 or 32 channels of analog data. Acquisition rates are up to 3000 samples/sec/channel.

The intermixed video and analog data are then transmitted through the bus of the host, plotted on the computer screen for real-time display, and stored on the mass storage device simultaneously in an interleaved format as a single file. The host computer also outputs an incrementing binary-coded time code at 10 sec intervals through one digital-to-analog channel (normally used for audio output on the host computer) to synchronize polygraph or other recordings.

Manipulation of Data Files

Data Analysis

An analytic program retrieves the physiological data and stores the data in IFFPHYS (Interleaved File Format, Physical Data; D. Sirag) format for analysis by a large number of previously developed routines. The IFFPHYS format is based on the EA IFF (Electronic Arts, Interleaved File Format) standard developed for interchange of data, including graphics, sound and text material, between different computer systems (Electronic Arts, San Jose, Calif.). The IFFPHYS specification provides for text comments, includes a description of byte orientation (i.e., orientation of most significant bit), and stores file placement indications of analog, event, and video data for analytic routines. Thus, a single file consists of alternating blocks of video and electrophysiological data together with other notations.

The analytic routines of the acquisition software and hardware allow real-time display of the video images above the electrophysiological data in a polygraph format, and allow transfer to other analytic routines for spectral, cross-correlation and other calculations. Since the video and analog data are stored together in one file, examination of the relationship of physiological characteristics to video signals is facilitated. Thus, a compressed display showing median heart rate across an 11 hr recording might indicate, for example, an anomaly 4 hours into the record. The corresponding video acquired at that time is displayed immediately.

Results

Two screen displays from a single image 4.5 sec period of 8 physiological input channels acquired with this procedure are shown in FIGS. 3, 4A and 4B.

The procedure acquires 8 channels of electrophysiological data, together with video images for prolonged periods of time. To save mass storage space, image acquisition can be reduced to rates appropriate for the study. Thus, acquisition at 3 to 15 fields/sec is frequently used for some infant studies where only body position is of concern. In cases where storage capacity is a less important issue, higher acquisition rates can be used to obtain smoother transitions between movements during review. An acquisition rate is necessary to achieve appropriate assessment of changes in the image.

General

An advantage of the procedure is storage of video and analog data in a standard file format, the IFFPHYS format. This format allows for storage of analog data with or without accompanying video, and provides a uniform format for analytic routines. In addition, considerable storage space can be saved by reducing the capture rate of the video signal. For circumstances which require little information on transient behaviors, such as determining prone or supine position for infant recordings, substantial reductions in image acquisition can be tolerated. Reduced image acquisition rates, however, obviously limit the temporal resolution for defining behavioral events.

The procedure allows rapid access to video images, and easy examination of associated physiological data with observed events. Simultaneous acquisition and data interleaving obviates the need to synchronize computer-acquired physiological data with video data stored on tape, and the considerable operator costs involved in such observational data correlation.

The procedure allows a degree of temporal synchronization (1/60 sec) which is difficult to achieve in conventional videotape acquisition without costly frame-accurate video recorders. The limitation of 8-bit resolution for the physiological signals can be easily overcome by compounding with a logarithmic amplifier to achieve extended dynamic range. However, the 8 bit (1 part in 256) resolution is comparable to the dynamic range of commercial instrumentation recorders, and judicious gain and offset settings will ensure adequate signal resolution.

The combined video-analog acquisition features provide substantial advantages when determination of the subject's behavior is of concern, or when correlation of physiological activity with behavior must be performed.

Assessment of cardiac activity following peripheral limb movements, evaluation of electroencephalographic signs during behaviors associated with seizures, and measurement of respiratory patterning in infants with particular head positions all comprise typical circumstances which would use this procedure effectively.

This procedure offers a solution for a costly aspect of long-term monitoring, that of determining subject behavior during particular electrophysiological events. Digital storage offers the capability of low-cost notation without observer fatigue, and allows a time resolution not attainable with human observation, since the data are stored in a form which is readily correlated with electrophysiological activity.

The system is of particular value when effective acquisition of video and physiological signals is necessary. The system obviates a need for a separate analog-to-digital converter circuit for computer data acquisition, since such a converter is provided in the video framegrabber.

A substantial benefit is the capability to store video and physiological signals simultaneously. This provides for rapid computer access to the interleaved data, without a need to align digitized information from separate sources. If computer storage is not required, the signals can be saved on videotape for later digitization.

The system described here is ideal for monitoring of infant sleep states and physiology in studies related to SIDS, for long-term monitoring of epileptic patients where both motor events and electrophysiological activity are of interest, and for studies of optical properties of tissue, where simultaneous video and electrophysiological signals are obtained.

Many other forms of the invention exist each differing from the other in matters of detail only.

Although the vertical band of the analog signal is represented in FIG. 3A as being towards the left-hand side of the video image, it is possible to move this vertical band to different positions of the video screen as required. Thus, it may be desirable to have the band portion on the right-hand side of the screen, or the center of the screen as necessary. This can depend on the portion of the video image that is required to be clearly visually seen. Additionally, the thickness of the band can be varied as desired. The narrower the band, the better is the video image. In situations where less than all of the horizontal lines are used for analog signals, the band may be represented by only a portion of the height of the video image. In such situations, the band can be located in a selected portion of the video screen as necessary. Thus, the representation of the analog signals can be chosen for location on the video screen as desired.

Any NTSC video digitizing board with the capacity for real time image acquisition can accomplish effective acquisition and processing of the video and analog signals.

Additionally, PAL video formats can also be used with a consequent reduction in temporal resolution to 50 samples per second.

In other situations with the buffering circuit the display of the analog data can be confined to half or less than the full height of the video screen. Thus if a slower refresh rate is required, there would be fewer inputs of analog data, since the 240 inputs would be used repetitively. Thus, for instance, if 120 analog event signals were used, each of the 240 data lines would be used twice, and the refresh would be twice as fast, namely 120 cycles/sec. This can be changed by various multiples as required. Also, although the invention has been described largely with regard to psychological data, there are clearly other applications. For instance, in scientific microscopy where video and analog data are obtained, the system will have useful advantages. Further, the video camera can be set up for microscopic viewing of tissues or events in a living or inanimate body.

The invention is to be determined solely in terms of the following claims.

We claim:

1. A system for processing multiple signals comprising:
   means for receiving a video signal representative of a camera image, the video signal being represented as multiple horizontal lines in a video frame,
   means for receiving multiple analog signals, the analog signals being representative of different analog inputs,
   means for digitally double buffering at least some of the analog signals, the means for buffering including means to effect repetition of analog signals within a single video image frame, the digital buffering includes means for repeating a sampling of the analog signals more than once within a single video frame and the digitization enhances recovery of the signal resolution of the analog signal with greater frequency and representation than an analog signal on a video signal,
   means for mixing the analog signals with the video signal whereby the analog signals are contained on at least some of the horizontal lines of the video frame, and
   means for outputting the mixed analog and video signals.

2. A system as claimed in claim 1 wherein the outputting means is selected from the group comprising at least one of a digitizer, and means for storing the mixed signals on a videotape, means for storing the mixed signals on a computer.

3. A system as claimed in claim 1 including means for representing the analog signals visually on a band in a visual video frame representation of the video signal.

4. A system as claimed in claim 3 wherein the band is composed of multiple horizontal signals, the multiple analog signals corresponding to at least part of the horizontal lines of the video signal.

5. A system as claimed in claim 4 wherein the intensity of the analog signal on a respective horizontal line is representative of the intensity of the analog signal.

6. A system as claimed in claim 1 wherein a single analog signal is contained on a single horizontal line.

7. A system as claimed in claim 3 wherein the band is a vertical band containing multiple analog signals on respective horizontal lines of the video frame, and wherein the band is located at a predetermined vertical position on the video frame.

8. A system as claimed in claim 1 wherein the video signal is represented by at least about 240 horizontal lines and wherein at least about 240 analog signals are inputted and mixed on respective horizontal lines.

9. A system as claimed in claim 1 wherein the video signal is represented by a predetermined first number of horizontal lines, and the analog signals are represented by a second predetermined number of signals, said second predetermined number being equal to the first predetermined number, or a lesser number of predetermined signals.

10. A system as claimed in claim 9 wherein the lesser number is a lesser multiple of the second number, selectively a half, a quarter, or an eighth of the second predetermined number.

11. A system as claimed in claim 1 including a screen for representing the video signals and the analog signals, and wherein a representation of the analog signals is depicted on the screen.

12. A system as claimed in claim 1 including means for receiving the analog signals in response to a horizontal trigger pulse representative of respective horizontal lines of a video signal.

13. A system as claimed in claim 1 including means for receiving physiological data as at least some of the analog signals or video signals.

14. A system as claimed in claim 1 wherein the double buffering includes means for reading out a signal from a first buffer, and means for reading analog signals into a second buffer, such that the analog signals are offset in time by at least one video frame.

15. A system as claimed in claim 1 including means for representing the analog signals on a selected portion of a video frame, and wherein the analog signals are represented on the video frame at a selectable, movable and variable location relative to the video frame of the video signals.

16. A system as claimed in claim 1 including means for obtaining a DC ground reference signal, said signal being at least one of the analog signals inputted to the mixing means, including means for varying at least some of the other analog signals in terms of the DC ground reference signal, and including means for feeding the ground reference signal to a differential amplifier for DC restoration.

17. A system for processing multiple signals comprising:
means for receiving a video signal representative of a camera image, and wherein the video signal is represented as multiple horizontal lines in a video frame,
means for receiving multiple analog signals, the analog signals being representative of different analog inputs,
means for digitizing the video signal,
means for digitizing the multiple analog signals,
means for subsequently effecting mixing receiving of the digitized multiple analog signals and the digitized video signal in an interleaved file format, and
means for parallel transmission of the digitized video signal and the digitized analog signals to a computer.

18. A system as claimed in claim 17 including means for storing the digitized video signal and digitized analog signal as a digital signal and including means for selectively processing the signal, such processing being selected to be from the group of at least one of means for storing the signal, means for analyzing the signal, and means for displaying the signal, such signal being the concurrent signal of the video and analog signals.

19. A method for processing multiple signals comprising:
receiving a video signal representative of a camera image, the video signal being represented as multiple horizontal lines in a video frame,
receiving multiple analog signals, the analog signals being representative of different analog inputs,
digitally double buffering at least some of the analog signals, the buffering including effecting repetition of analog signals within a single video image frame, the digital buffering including repeating a sampling of the analog signals more than once within a single video frame, and the digitization enhancing recovery of the dynamic resolution of the analog signal;
mixing the analog signals with the video signal whereby the analog signals are contained on at least some of the horizontal lines of the video frame, and
outputting the mixed analog and video signals.

20. A method as claimed in claim 19 wherein the outputting is selected from the group comprising at least one of a digitizing, storing the mixed signals on a videotape, means for storing the mixed signals on a computer.

21. A method as claimed in claim 19 including representing the analog signal visually on a band in the visual representation of the video signal.

22. A method as claimed in claim 21 wherein the band is a vertical band containing multiple analog signals on respective horizontal lines of the video image, and wherein the band is located at a predetermined vertical position on the video image.

23. A method as claimed in claim 19 including receiving the analog signals in response to a horizontal trigger pulse representative of respective horizontal lines of a video signal.

24. A method as claimed in claim 19 including receiving physiological data as at least some of the analog signals or video signals.

25. A method as claimed in claim 19 including wherein the double buffering includes reading out from a first buffer and reading analog signals into a second buffer such that the analog signals are offset in time by at least one video frame.

26. A method for processing multiple signals comprising:
receiving video signals representative of a camera image, and wherein the video signal is represented as multiple horizontal lines in a video frame,
receiving multiple analog signals, the analog signals being representative of different analog inputs,
digitizing the video signal,
digitizing the multiple analog signals,
digitally double buffering at least some of the analog signals, and
subsequently effecting mixing of the digitized multiple analog signals and the digitized video signal, the mixing being effected in an interleaved file format.

27. A method as claimed in claim 26 including storing the digitized video signal and digitized analog signal as a digital signal.

28. A system for processing multiple signals comprising:
means for receiving a video signal representative of a camera image, the video signal being represented as multiple horizontal lines in a video frame,
means for receiving multiple analog signals, the analog signals being representative of different analog inputs, the video signal being represented by a predetermined first number of horizontal lines, and the analog signal is represented by a second predetermined number of signals, said second predetermined number being less than the first predetermined number, the lesser number being representative of a multiple sampling of each analog signal within each video frame, means for digital double buffering at least some of the analog signals, means for mixing the analog signals with the video signal whereby the analog signals are contained on at least some of the horizontal lines of the video frame, and means for outputting the mixed analog and video signals.

29. A system as claimed in claim 28 including means for representing the analog signals visually on a band in a visual video frame representation of the video signal.

30. A system as claimed in claim 29 wherein the band is composed of multiple horizontal signals, the multiple analog signals corresponding to at least part of the horizontal lines of the video signal.

31. A system as claimed in claim 30 wherein the intensity of a respective horizontal line is representative of the intensity of the analog signal.

32. A system for processing multiple signals comprising:

means for receiving a video signal representative of a camera image, the video signal being represented as multiple horizontal lines in a video frame, means for receiving multiple analog signals, the analog signals being representative of different analog inputs, means for double buffering at least some of the analog signals, the means for buffering including means to effect repetition of analog signals within a single video image frame, the buffering means including means for repeating a sampling of the analog signals more than once within a single video frame, and the double buffering enhancing temporal recovery of the analog signals and amplitude resolution of the analog signals, such enhanced temporal recovery being such that double buffering includes means for a multiple sampling of analog signals and reading out from a first buffer and means for reading analog signals into a second buffer such that the analog signals are offset in time by at least one video frame;

means for mixing the analog signals with the video signal whereby the analog signals are contained on at least some of the horizontal lines of the video frame, and means for outputting the mixed analog and video or more signals.

33. A system for processing multiple signals comprising:

means for receiving an analog video signal representative of a camera image, the video signal being represented as multiple horizontal lines in a video frame, means for receiving multiple analog signals, the analog signals being representative of different analog inputs, means for digital buffering at least some of the analog signals, the means for digital buffering including means to effect repetition of analog signals within a single video image frame, and the buffering enhancing recovery of the signal resolution of the analog signal, such enhanced recovery including means for permitting mixing of the analog signals with video frame at a rate faster than the analog signals;

means for mixing the analog signals with the video signal whereby the analog signals are contained on at least some of the horizontal lines of the video frame as intensity encoded values of at least some of the video pixels, and means for outputting the mixed analog and video signals.

34. A system as claimed in claim 33 including means for digitizing the analog signals prior to mixing the analog signal and the video signal.

35. A system as claimed in claim 33 including means for digitizing the analog signals prior to directing the signal to the buffering means, and means for converting the buffered signal back to an analog signal prior to mixing the analog signal and the video signal in the mixing means.

* * * * *